United States Patent
Modglin

(10) Patent No.: US 7,322,950 B2
(45) Date of Patent: Jan. 29, 2008

(54) PROCESS FOR MANUFACTURE OF LAMINATE SHELLS

(75) Inventor: Michael D. Modglin, Braselton, GA (US)

(73) Assignee: DeRoyal Industries, Inc., Powell, TN (US)

( * ) Notice: Subject to any disclaimer, the term of this patent is extended or adjusted under 35 U.S.C. 154(b) by 49 days.

(21) Appl. No.: 11/419,065

(22) Filed: May 18, 2006

(65) Prior Publication Data

US 2006/0200059 A1    Sep. 7, 2006

Related U.S. Application Data

(63) Continuation-in-part of application No. 11/353,825, filed on Feb. 14, 2006, which is a continuation-in-part of application No. 10/738,796, filed on Dec. 17, 2003, now Pat. No. 7,025,737.

(60) Provisional application No. 60/437,853, filed on Jan. 3, 2003.

(51) Int. Cl.
A61F 5/00 (2006.01)

(52) U.S. Cl. .............................. 602/5; 602/19

(58) Field of Classification Search .............. 602/5, 602/19; 128/96.1, 100.1, 102.1, 106
See application file for complete search history.

(56) References Cited

U.S. PATENT DOCUMENTS

| | | | |
|---|---|---|---|
| 2,800,129 A | 7/1957 | Swaay | |
| 3,756,226 A | 9/1973 | Calabrese et al. | |
| 3,945,376 A | 3/1976 | Kuehnegger | |
| 3,957,040 A | 5/1976 | Calabrese | |
| 4,080,962 A | 3/1978 | Berkeley | |
| 4,178,923 A | 12/1979 | Curlee | |
| 4,285,336 A | 8/1981 | Oebser et al. | |
| 4,289,122 A | 9/1981 | Mason et al. | |
| 4,413,619 A | 11/1983 | Garth | |
| 4,475,543 A | 10/1984 | Brooks et al. | |
| 4,502,471 A | 3/1985 | Owens | |
| 4,508,110 A | 4/1985 | Modglin | |
| 4,515,153 A | 5/1985 | Calabrese | |

(Continued)

FOREIGN PATENT DOCUMENTS

DE    4211077    10/1993

(Continued)

OTHER PUBLICATIONS

The University of Iowa, Virtual Hospital: Pelvis & Perineum: Image: Iliac Crest 1992-2003 http://www.vh.org/adult/provider/radiology/pelvis/Lateral109.html.

Primary Examiner—Michael A. Brown
(74) Attorney, Agent, or Firm—Luedeka, Neely & Graham, PC

(57) ABSTRACT

An orthosis may be made by providing a laminate material having a flexible foam material and a substantially rigid plastic sheet material sandwiched between a pair of soft flexible sheet materials. A body support is formed by heating the laminate material under conditions of pressure to soften the laminate to a pliable state, cutting the laminate to a desired shape to yield a pattern corresponding to a desired shape of the body support, providing a form corresponding to a desired configuration of the body support and positioning the pattern on the form in a pliable state, applying a negative pressure to conform the pattern.

10 Claims, 9 Drawing Sheets

U.S. PATENT DOCUMENTS

| | | |
|---|---|---|
| 4,602,442 A | 7/1986 | Revill et al. |
| RE32,219 E | 8/1986 | Garth |
| 4,677,969 A | 7/1987 | Calabrese |
| 4,778,717 A | 10/1988 | Fitchmun |
| 4,886,052 A | 12/1989 | Calabrese |
| 4,976,257 A | 12/1990 | Akin et al. |
| D314,623 S | 2/1991 | Calabrese et al. |
| 4,993,409 A | 2/1991 | Grim |
| 5,012,798 A | 5/1991 | Graf et al. |
| 5,054,475 A | 10/1991 | Calabrese et al. |
| 5,072,725 A | 12/1991 | Miller |
| 5,097,824 A | 3/1992 | Garth |
| 5,180,361 A | 1/1993 | Moore et al. |
| 5,230,698 A | 7/1993 | Garth |
| 5,344,391 A | 9/1994 | Modglin |
| 5,437,612 A | 8/1995 | Moore et al. |
| 5,474,523 A | 12/1995 | Miller |
| 5,503,621 A | 4/1996 | Miller |
| 5,573,501 A | 11/1996 | Ruscito et al. |
| 5,620,412 A | 4/1997 | Modglin |
| 5,622,529 A | 4/1997 | Calabrese |
| 5,632,722 A | 5/1997 | Tweardy et al. |
| 5,688,229 A | 11/1997 | Bauer |
| 5,765,224 A | 6/1998 | Johnson |
| 5,797,713 A | 8/1998 | Tweardy et al. |
| 5,833,638 A | 11/1998 | Nelson |
| 5,853,378 A | 12/1998 | Modglin |
| 5,911,697 A | 6/1999 | Biedermann et al. |
| 5,967,998 A | 10/1999 | Modglin |
| 6,067,665 A | 5/2000 | DePalma et al. |
| 6,071,255 A | 6/2000 | Calabrese |
| 6,102,879 A | 8/2000 | Christensen et al. |
| 6,146,349 A | 11/2000 | Rothschild et al. |
| 6,213,968 B1 | 4/2001 | Heinz et al. |
| 6,254,560 B1 | 7/2001 | Tweardy et al. |
| 6,267,741 B1 | 7/2001 | Lerman |
| 6,270,469 B1 | 8/2001 | Mott |
| 6,315,746 B1 | 11/2001 | Garth et al. |
| 6,478,759 B1 | 11/2002 | Modglin et al. |
| 6,503,217 B1 | 1/2003 | Gibbs et al. |
| 6,666,838 B2 | 12/2003 | Modglin et al. |
| 6,676,617 B1 | 1/2004 | Miller |
| 6,776,767 B2 | 8/2004 | Reinecke et al. |
| 6,893,411 B1 | 5/2005 | Modglin |
| 6,899,689 B1 | 5/2005 | Modglin |
| 6,926,685 B1 | 8/2005 | Modglin |
| 7,025,737 B2 | 4/2006 | Modglin |
| 2003/0073942 A1 | 4/2003 | Gibbs et al. |

FOREIGN PATENT DOCUMENTS

| | | |
|---|---|---|
| EP | 0253335 | 1/1988 |
| WO | WO 01/37764 | 5/2001 |
| WO | WO 02/00147 | 1/2002 |

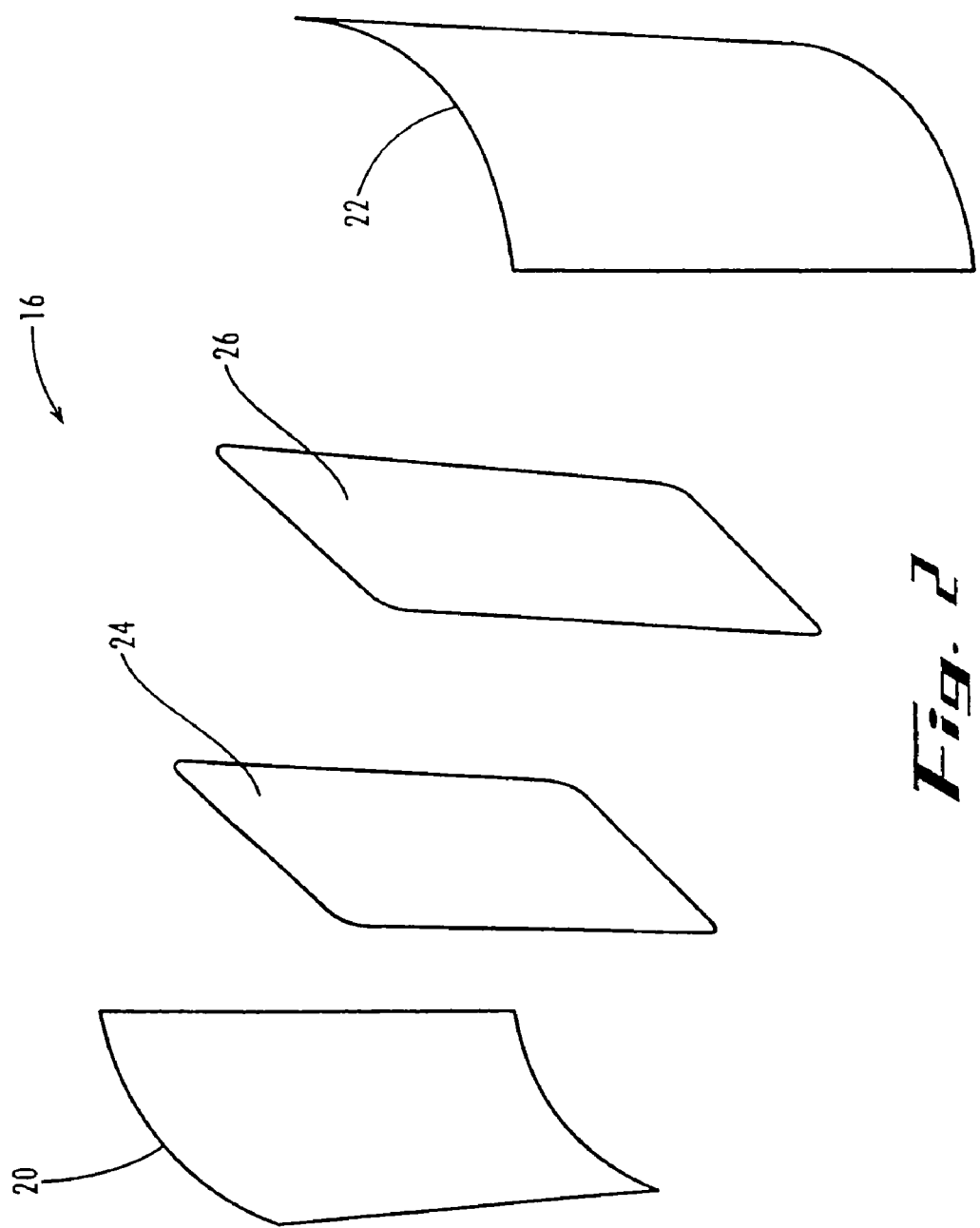

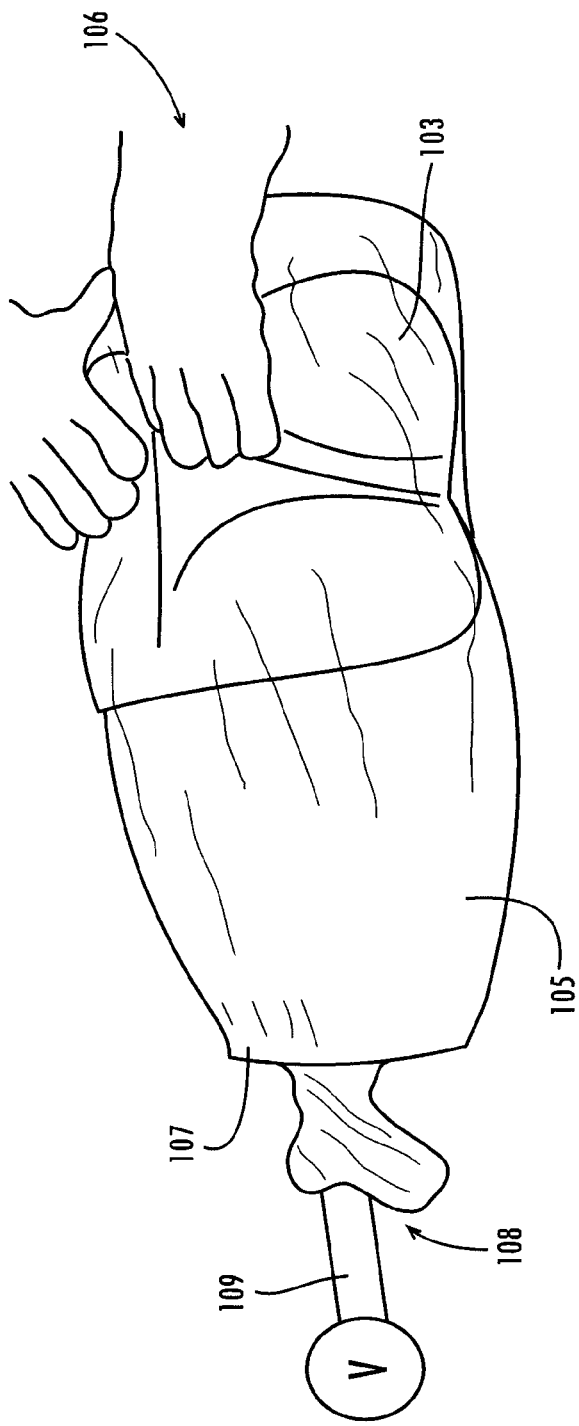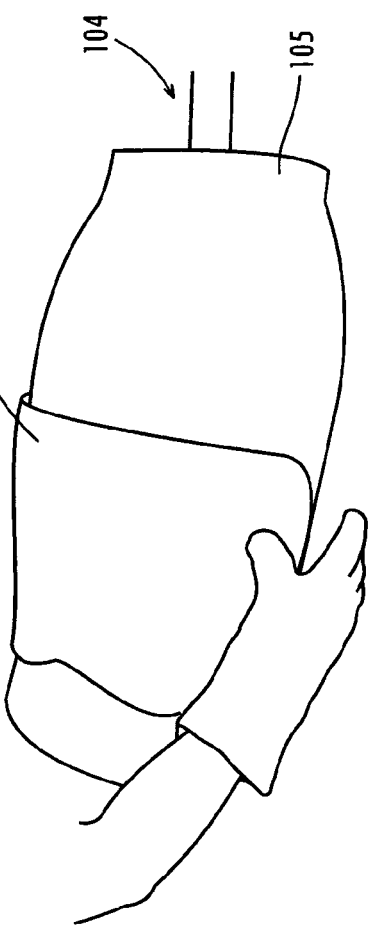
Fig. 10
Fig. 9

PROCESS FOR MANUFACTURE OF LAMINATE SHELLS

CROSS-REFERENCE TO RELATED APPLICATION

This is a continuation-in-part of U.S. application Ser. No. 11/353,825, filed Feb. 14, 2006, and entitled "Spinal Brace Having Laminate Shells," which is a continuation-in-part of (Allowed) U.S. application Ser. No. 10/738,796, filed Dec. 17, 2003 now U.S. Pat. No. 7,025,737, and entitled "Spinal Brace Having Overlapping Rigid Members," which is a continuation-in-part of provisional patent application Ser. No. 60/437,853, filed Jan. 3, 2003, and entitled "Spinal Brace Having Overlapping Rigid Members."

FIELD OF THE INVENTION

This invention relates generally to methods for producing medical orthoses. More particularly, this invention relates to the production of laminate shells for spinal braces. The shells have sufficient rigidity to serve a support function, yet which do not unduly constrict breathing of the patient wearing the brace and offer improved comfort.

BACKGROUND AND SUMMARY OF THE INVENTION

Improvement is desired in the field of spinal braces. Braces are typically constructed using rigid materials, such as being formed by vacuum molding plastic. Such braces have good support characteristics, but, are disadvantageous in that they are relatively heavy and may constrict respiration of the patient and be uncomfortable to wear.

The disclosure relates to a process for the manufacture of improved orthosis, particularly spinal orthosis, that are relatively lightweight and supportive, and which are believed to offer improved comfort and reduced constriction of respiration as compared to conventional spinal braces.

In a preferred embodiment, the process includes the steps of providing a laminate material having a flexible foam material and a substantially rigid plastic sheet material sandwiched between a pair of soft flexible sheet materials. A body support is formed by heating the laminate material under conditions of pressure to soften the laminate to a pliable state, cutting the laminate to a desired shape to yield a pattern corresponding to a desired shape of the body support, providing a form corresponding to a desired configuration of the body support and positioning the pattern on the form in a pliable state, applying a negative pressure to conform the pattern.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

FIG. 2 is an exploded view of a laminate material used in the brace of FIG. 1

FIG. 3 is an exterior plan view of a posterior support of the brace of FIG. 1.

FIGS. 7-11 show steps in a process for forming the laminate material into the posterior and anterior supports.

DETAILED DESCRIPTION

Figure 1:
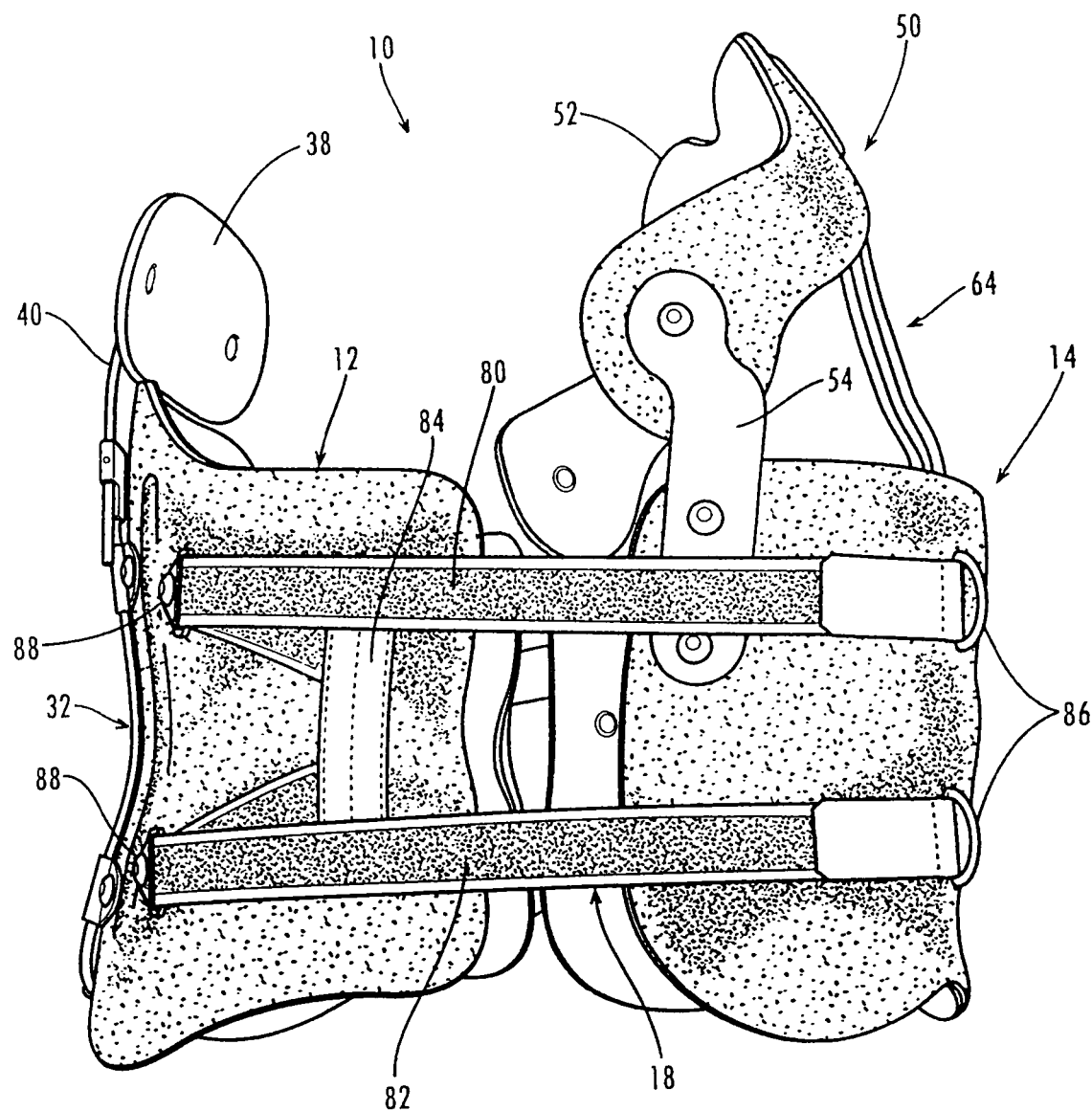
FIG. 1 is a perspective side view of a spinal brace made utilizing laminate shells produced in accordance with a preferred embodiment of the disclosure.
Figure 1:
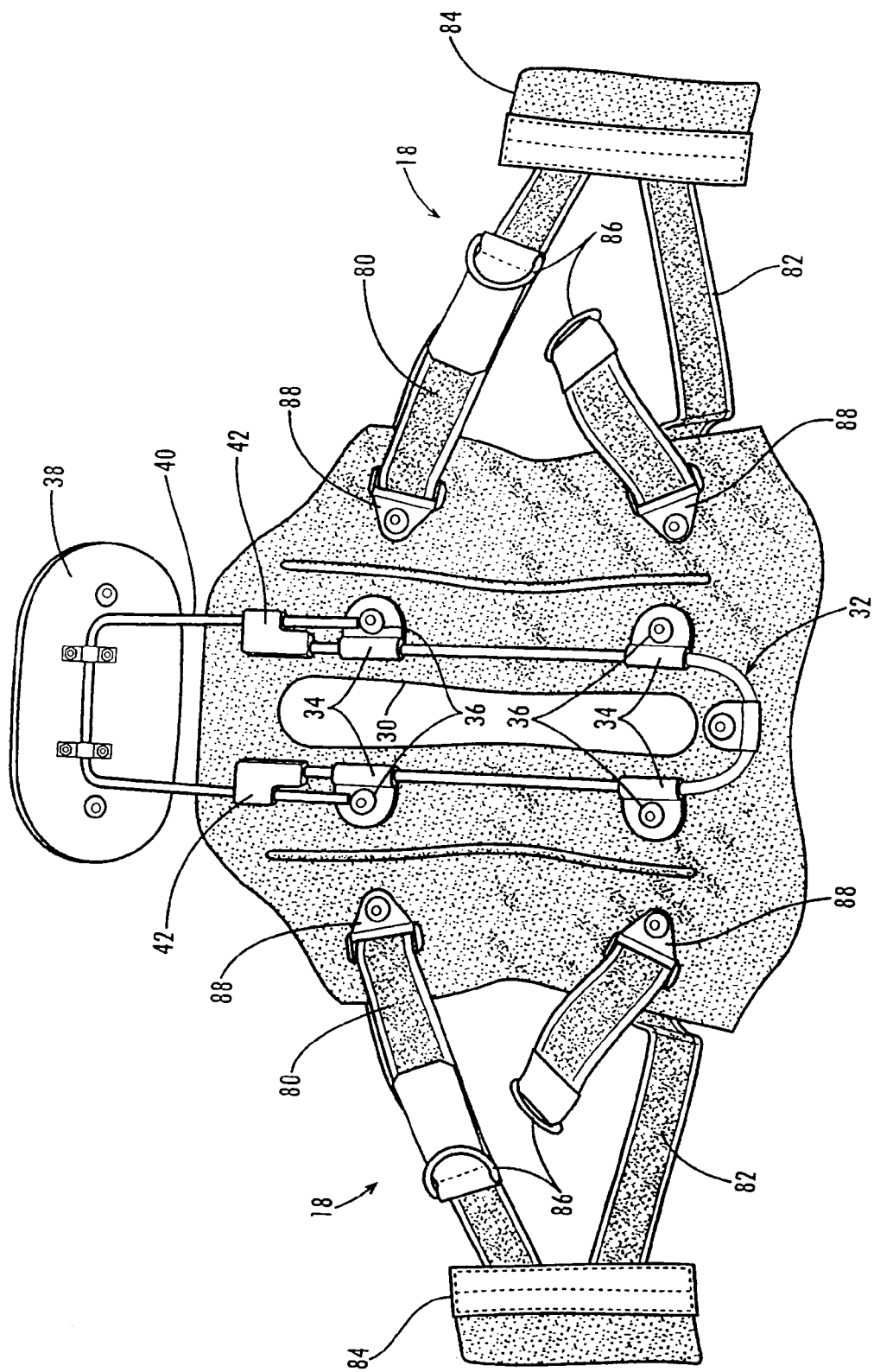

With reference to the drawings, the invention relates to the manufacture of a spinal brace 10 particularly configured to serve as a thoracic-lumbar-sacral orthosis (TLSO). The brace 10 includes a posterior support 12 and an anterior support 14. The supports 12 and 14 are each made of a laminate material 16 (FIG. 2) that enables the supports 12 and 14 to have sufficient rigidity to serve a support function, yet to be relatively lightweight and to avoid undue constriction of breathing of the patient wearing the brace. The brace 10 also preferably includes a pair of strap assemblies 18. The brace 10 is preferably positioned on a patient while supine.

It will be understood that the brace 10 may be otherwise configured for providing an orthosis suitable for treating other portions of the spine, such as the cervical portions, as well as fewer portions, such as a configuration as a lumbar-sacral orthosis (LSO). The brace 10 may also be configured to impart a particular orientation, such as a flexion, extension, or a neutral orientation to the spine.

The supports 12 and 14 are each preferably of lightweight laminate construction and have sufficient rigidity to serve a support function, while also having a degree of flexibility sufficient to permit substantially unrestricted contractions and expansions of the torso of the user associated with breathing.

With reference to FIG. 2, the supports 12 and 14 each include an interior or patient engaging surface 20 and an exterior surface 22. The surfaces 20 and 22 are preferably each made of a soft material that is capable of engaging hook material in the context of mating hook and loop materials, such as VELCRO. However, other soft, preferably fabric materials may be used. Sandwiched between the surfaces 20 and 22 is a foam material 24 and a plastic sheet 26, with such components being bonded to one another to form a unitary laminate material.

The foam material 24 is preferably a sheet of about ⅛ inch thick closed cell foam material. The sheet 26 is preferably a sheet of about 1/16 inch thick low density polyethylene. The components of the supports 12 and 14 are preferably bonded to form the laminate material as by vacuum molding with adhesive placed between each layer. Alternatively, the supports are made by flame lamination without the use of adhesive. In flame lamination, the layers are passed over an open flame to partially melt the foam to create a thin layer of molten polymer. The molten polymer serves to adhere the materials together on both sides of the foam. The supports may be heated if desired, as by a heat gun or oven, to soften them so that they may be custom fit to the patient. However, a particularly preferred method for configuring the supports 12 and 14 made of the laminate 16 is described below in connection with FIGS. 7-11.

Figure 4:
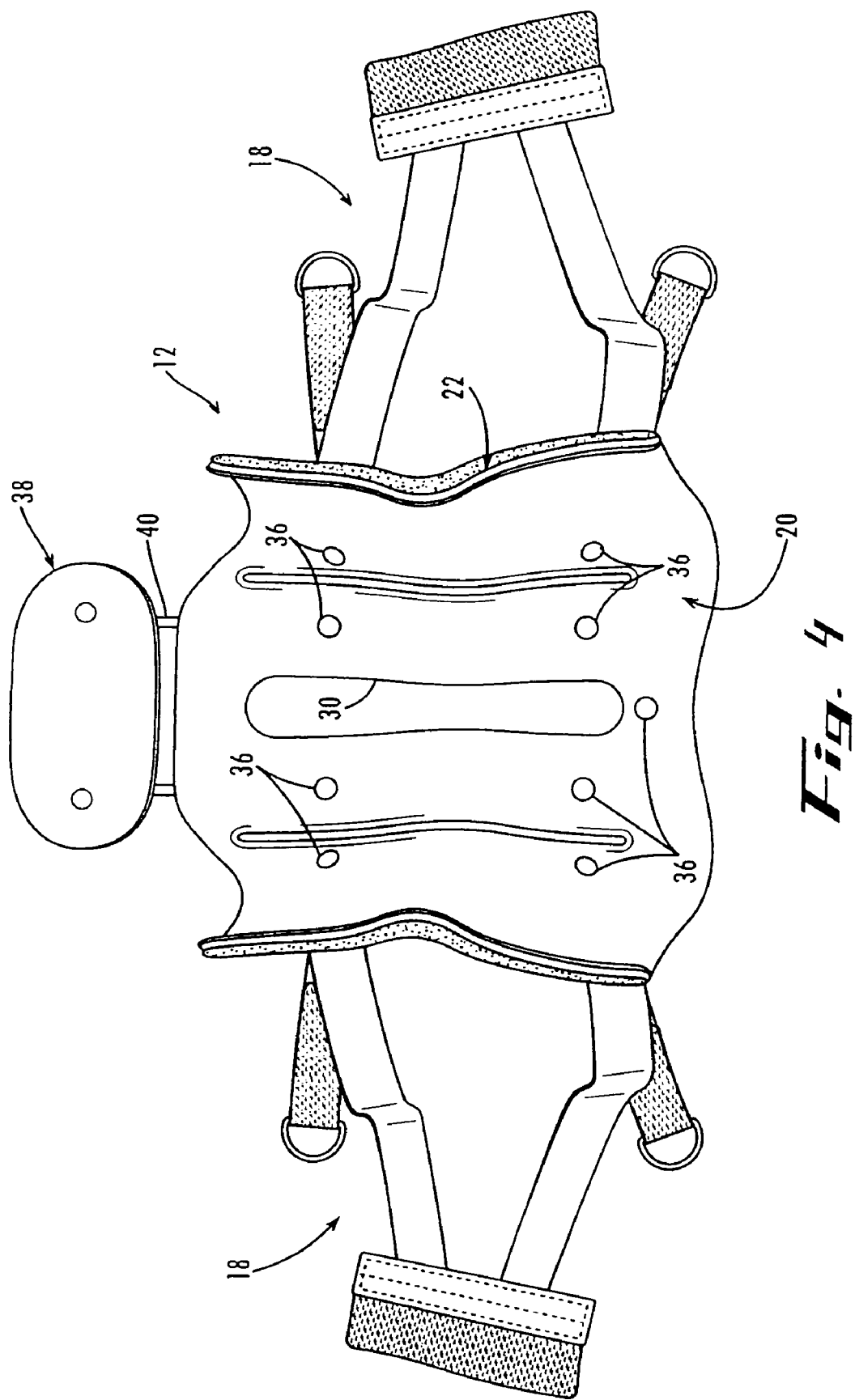
FIG. 4 is an interior plan view of the posterior support of FIG. 3.

With additional reference to FIGS. 3 and 4, the posterior support 12 is made of the laminate 16 and generally shaped to conform to and wrap around a posterior portion of a patient. An elongate aperture 30 is provided on the support at a central location corresponding to the location of the spinal column of a patient. The support 12 may include additional rigidifying structure adjacent the aperture 30 to rigidify the support at locations immediately lateral the spinal column of the user. This may be accomplished as by incorporating additional rigidifying materials within the laminate, such as rigid strips of ABS plastic, along both sides of the aperture 30. Alternatively, as seen in FIG. 3, this may be accomplished by including an external rigidifying member 32.

The rigidifying member 32 preferably provides additional rigidity along the sides of the aperture 30 and may be provided as rigid members such as aluminum or composite rods or the like. In FIG. 3 the rigidifying member 32 is provided by an aluminum rod configured to be substantially U-shaped and secured to the support as by clamps 34 affixed to the support 12 using fasteners 36, such as plastic screws or rivets. The use of aluminum rods, or other rigid yet malleable material, is desirable in that it may be adjusted to correspond to desired kyphotic or lordotic curves. For example, it may be desirable to shape the rigidifying member 32 to impart desired curves to regions of the spinal column and to periodically change these curves.

The support 12 may also include a thoracic support 38 extending above and adjustably positionable relative to the support 12 for supporting the kyphotic curve imparted to the thoracic region of the spinal column. The support 38 may be made of the laminate 16 and may be mounted relative to the support 12 as by use of a U-shaped portion of an aluminum rod 40 adjustably securable to mounting blocks 42 located on the upright ends of the rigidifying member 32. Alternatively, individual or separate sections of aluminum rods may be used to provide the support 38.

Figure 5:
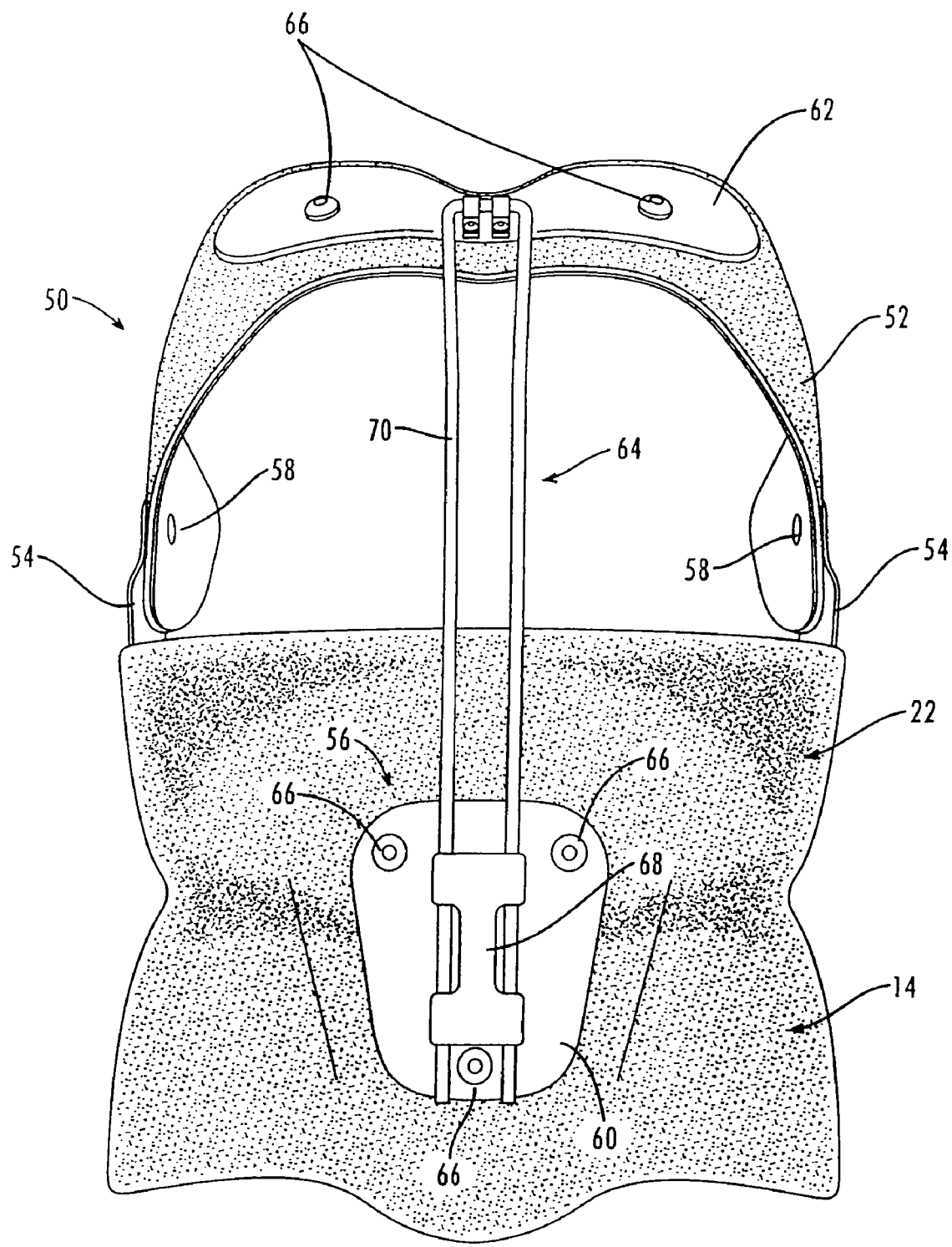
FIG. 5 is an exterior plan view of an anterior support of the brace of FIG. 1.
Figure 6:
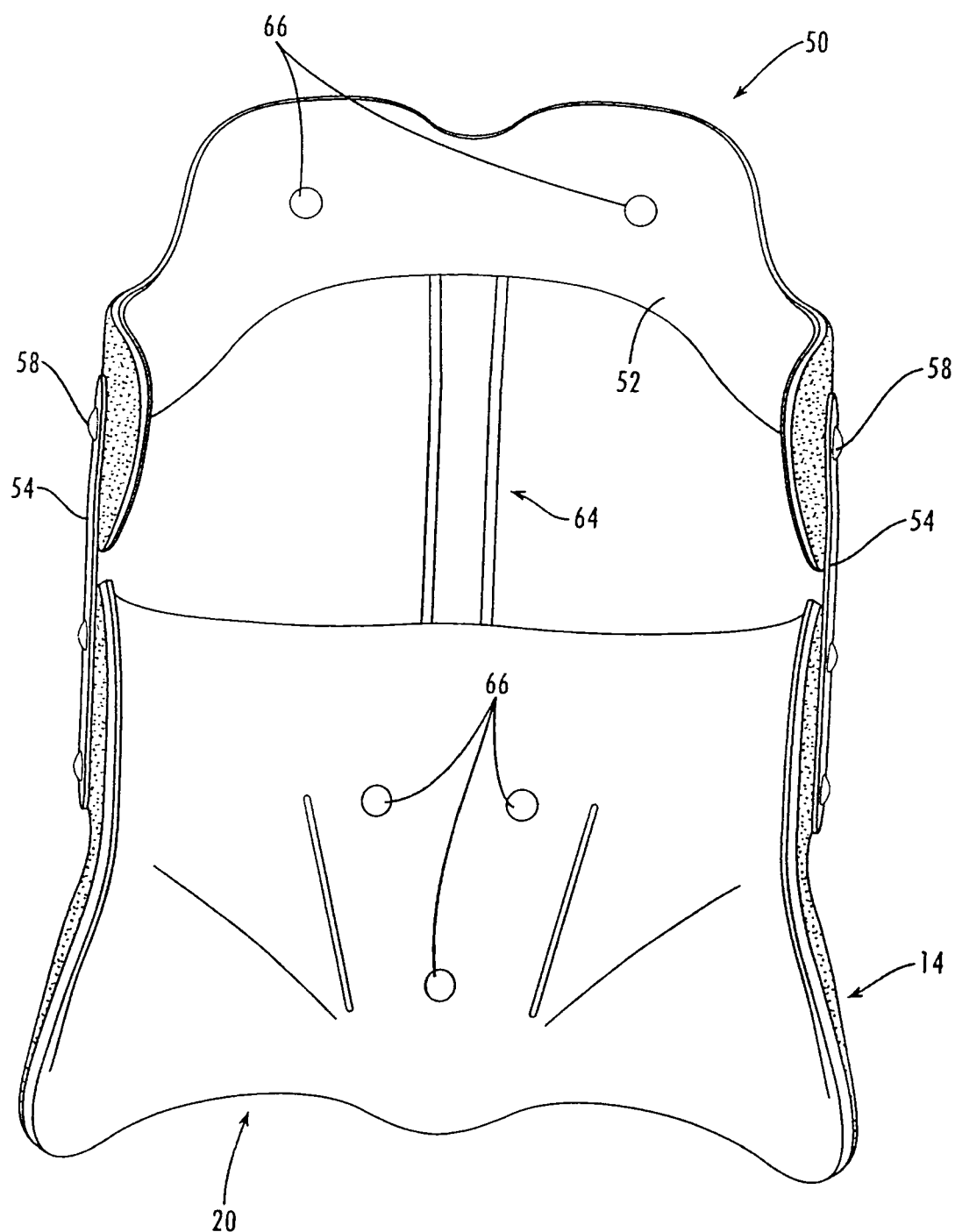
FIG. 6 is an interior plan view of the anterior support of FIG. 5.
Figure 7:
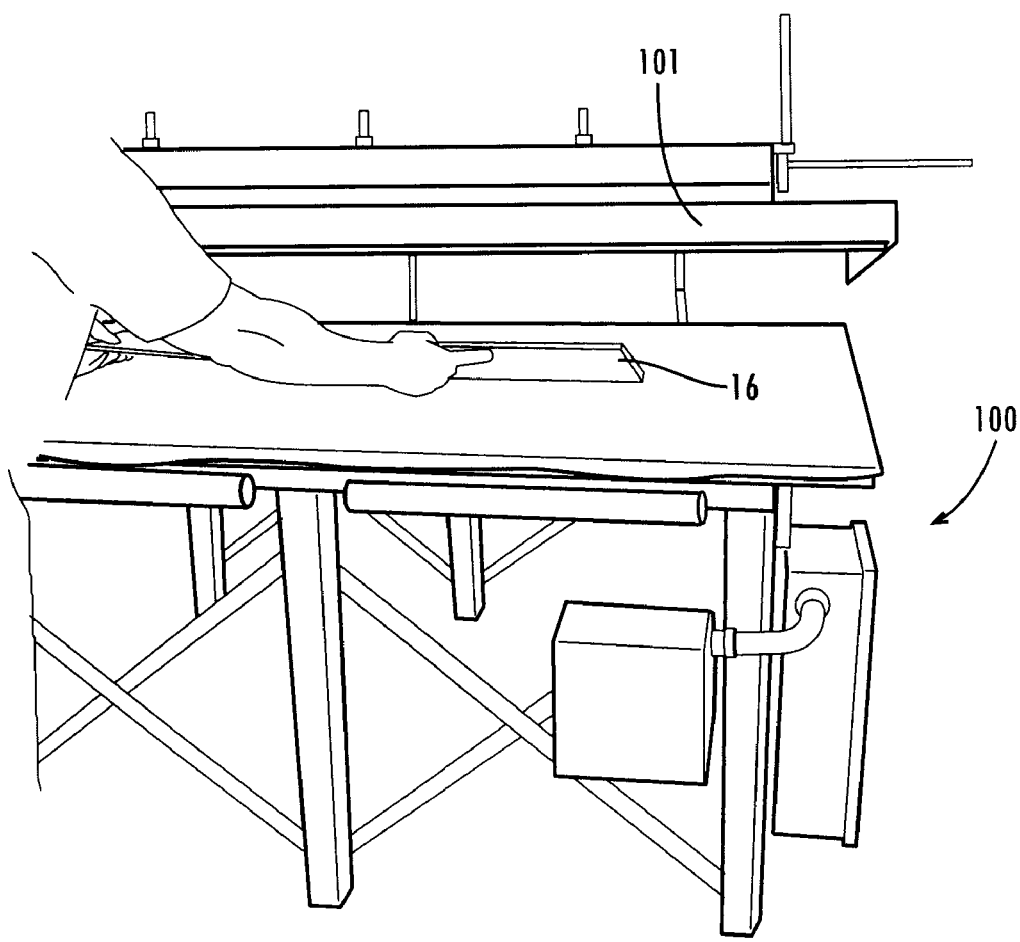
Figure 8:
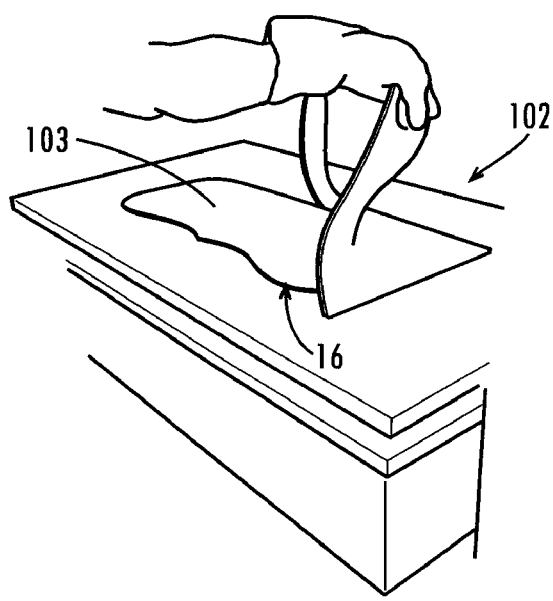
Figure 11:
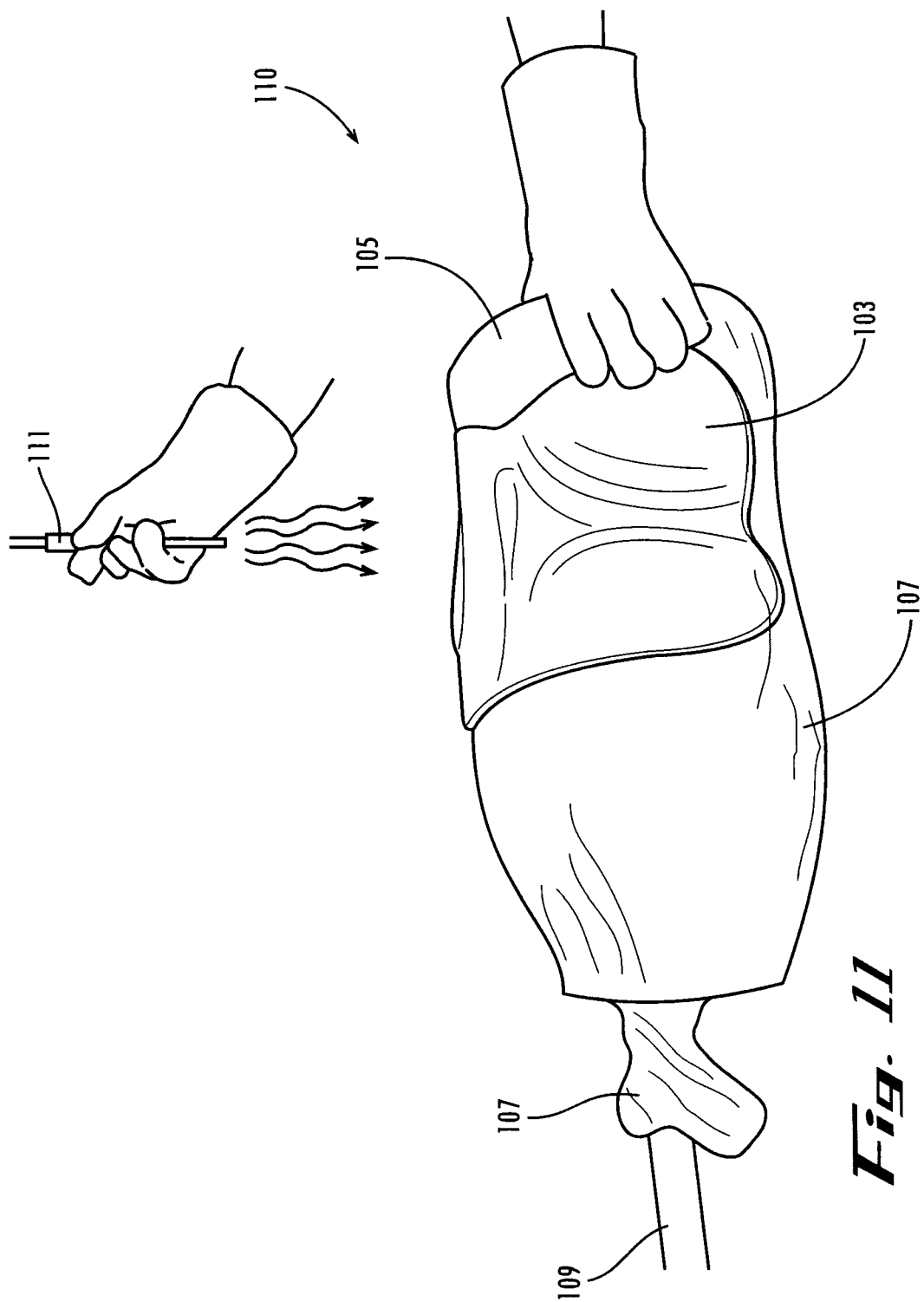

With additional reference to FIGS. 5 and 6, the anterior support 14 is made of the laminate 16 and is generally shaped to conform to and wrap around a anterior portion of a patient, and to slightly overwrap the edges of the anterior support 12. If desired, a sternal pad system 50 may be attached to the anterior support 14 for limiting flexion or for hyperextending the upper thoracic region of a patient. The sternal pad system 50 includes a pad member 52, a pair of side mounting members 54, and a central adjustable mounting system 56.

The pad member 52 is preferably made of the laminate 16. The pad member 52 is substantially U-shaped and configured for cradling the sternum of a user. The side mounting members 54 are preferably provided by elongate strips of a rigid plastic material, such as ABS plastic, and configured to be statically or adjustably positioned. For example, an upper end of the mounting members 54 is preferably angled so that they can be reversed to change the mounted position or angle of the pad member 52 relative to the support 14. The mounting members 54 are preferably secured to the support 14 and the pad member 52 as by fasteners 58, most preferably adjacent the exposed edges of the support 14 and the pad member 52.

The central adjustable mounting system 56 (FIG. 5) preferably includes a support mounting plate 60, a pad member mounting plate 62, and a rigid extension 64 that spans between the plate 60 and the plate 62. Fasteners 66 may be used to mount the plates 60 and 62, the plates 60 and 62 preferably being made of a lightweight plastic material, such as ABS plastic. The plate 60 preferably mounts to a central portion of the support 14 and includes a mounting block 68 for adjustably receiving the extension 64. In this regard, the extension 64 may be provided as by a U-shaped portion of an aluminum rod 70 adjustably securable to the mounting block 68 so as to permit adjustment of the height of the pad member 52 relative to the support 14. Also, the rod 70 may be shaped to adjust the position of the pad member 52. The central portion of the U-shaped rod 70 is preferably secured to the plate 62 as by fasteners or the like.

The strap assemblies 18 each preferably include first and second straps 80 and 82 connected at common ends to a common securement strap 84 having a hook material on the interior surface thereof so as to be positionable in releasable engagement with the exterior surface 22 of the laminate 16 of the anterior support 14, as seen in FIG. 1. The opposite free ends of the straps 80 and 82 include a hook material on the interior surface thereof so as to be positionable in releasable engagement with the exterior surface 22 of the laminate 16 of the anterior support 12. D-rings 86 or the like may be located on the ends of the straps 80 and 82 to facilitate grasping thereof. Slides or chafes 88 are preferably secured to the exterior of the posterior support 12, with the straps 80 and 82 passed therethrough.

To install the brace 10, the user places the posterior support 12 around the posterior body portions and, while holding this in place, places the anterior support 14 over the anterior body portions, and slightly overlapping the anterior support 12. This process is facilitated by having one of the strap assemblies secured to both of the supports 12 and 14. Next, the user may secure both of the strap assemblies 18 by pressing the securement straps 84 into firm engagement with the surface 22 of the posterior support, and then pulling on the D-rings 86, one at a time or two at a time, and then securing the hook material associated with such ends in engagement with the loop material of the exterior surface 22 of the anterior member 14. The user may adjust the compression and fit of the brace 10 by adjusting the locations and orientations of the securement straps 84 or the opposite free strap ends, or both.

In accordance with another aspect of the disclosure, there is described a preferred process for configuring the laminate 16 into the supports 12 and 14. The process advantageously enables the laminate 16 to be formed, while avoiding undesirable delamination of the laminate and wrinkling of the patient engaging surfaces 20 and 22. The process is substantially the same for the supports 12 and 14. Thus, the process will be described only in connection with manufacture of the support 14.

With reference to FIGS. 7-11, the process includes a step 100 in which the laminate 16 used to provide the support 14 is heated under conditions of pressure to soften the laminate 16. Step 100 is preferably accomplished as by use of a heated press 101 of the type commonly used to apply decals and the like to t-shirts and other clothing. For this step, the laminate 16 is preferably subjected to a temperature of from about 285 to about 310° F. at a light pressure to inhibit wrinkling for a time period of from about 4 to about 8 minutes.

In step 102, the heated and pliable laminate from step 100 is cut to a pattern 103 corresponding to the support 14 and the excess material recycled or otherwise disposed. Cutting of the laminate to the desired pattern 103 is preferably accomplished as by use of a die-cut press or stamp press or the like having a continuous knife edge that is pressed against the material to be cut in the manner of a cookie cutter to provide the desired outline or pattern to the laminate 16. Step 102 is preferably accomplished relatively quicky so that the pattern 103 remains in a substantially pliable state. It has been observed that the laminate 16 from step 100 remains substantially pliable for a time period of up to about 6 minutes, which time has been observed to be sufficient to accomplish all of the process steps described herein. Alternatively, it will be understood that the laminate may be cut into the pattern prior to heating it per step 100.

In step 104, the pliable pattern 103 is positioned on a form 105 corresponding to the body portion with which the support 14 is to be used. As will be understood, the form 105 may be of various dimensions and may be a standard form or a custom form corresponding to a specific patient. The form 105 is preferably a hard foam or a hollow plastic form having a solid and relatively hard surface. However, as described below, the form 105 may be configured to have a plurality of small apertures in the region where the pattern 103 is to be applied for application of negative pressure for forming the pattern 103 into the desired shape for the support 104.

In step 106, an airtight and flexible enclosure, such as a plastic bag 107 is placed around the form 105 having the pattern 103 thereon. An open end 108 of the bag 107 is sealingly secured around a vacuum hose 109 located to extend into the open end 108 of the bag 107. The hose 19 is connectable to a vacuum source V for supplying a negative pressure to the interior of the bag 107. Under the conditions of negative pressure within the bag 107, the pattern 103 is snugly conformed to the shape of the portion of the form 105 against which it is positioned. The vacuum source V preferably supplies a negative pressure of from about −10 to about −20 inch pounds mercury and this pressure is preferably maintained for a time period of from about 4 to about 6 minutes. Alternatively, the form 105 may be configured to have a plurality of small apertures in the region where the pattern 103 is to be applied. The end of the form 105 would be closed, except for a passage for the hose 109 for application of negative pressure for forming the pattern 103 into the desired shape for the support 104.

In step 110, the pattern 103 is cooled to a non pliable state negative pressure is applied to conform it to the form. For example, cooling fluid, such as air is applied, preferably by an exterior fluid supply, such as an air hose 111, to cool the pattern 103 while negative pressure is applied via the hose 109. For example, relatively cool air is supplied from a compressed air source as by spraying the air over the pattern 103 for a time sufficient to cool it so that it retains the formed shape.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A method for making a spinal orthosis, the method comprising the steps of:

providing a first laminate material comprising a flexible foam material and a substantially rigid plastic sheet material sandwiched between a pair of soft flexible sheet materials and bonded together to yield a unitary and substantially rigid first laminate material;

forming an anterior support from the first laminate material, the anterior support being formed by heating the first laminate material under conditions of pressure to soften the first laminate to a pliable state, cutting the first laminate to a desired shape to yield a first pattern corresponding to a desired shape of the anterior support, providing a first form corresponding to a desired configuration of the anterior support and positioning the first pattern on the first form in a pliable state, applying a negative pressure to conform the first pattern to the first form, and cooling the conformed first pattern to yield the anterior support;

providing a second laminate material comprising a flexible foam material and a substantially rigid plastic sheet material sandwiched between a pair of soft flexible sheet materials and bonded together to yield a unitary and substantially rigid second laminate material;

forming an posterior support from the second laminate material, the posterior support being formed by heating the second laminate material under conditions of pressure to soften the second laminate to a pliable state, cutting the second laminate to a desired shape to yield a second pattern corresponding to a desired shape of the posterior support, providing a second form corresponding to a desired configuration of the posterior support and positioning the second pattern on the second form in a pliable state, applying a negative pressure to conform the second pattern to the second form, and cooling the conformed second pattern to yield the posterior support.

2. The method of claim 1, wherein the step of cutting the first laminate occurs prior to the step of heating the first laminate under conditions of pressure.

3. The method of claim 1, wherein the step of cutting the first laminate occurs after the step of heating the first laminate under conditions of pressure.

4. The method of claim 1, wherein the step of applying a negative pressure to conform the first pattern to the first form, comprises applying a plastic bag around the first form having the first pattern thereon and applying a negative pressure to the bag.

5. The method of claim 1, wherein the anterior and posterior support members are configured for placement around a torso of a user and have sufficient rigidity to serve a support function, while also having a degree of flexibility sufficient to permit substantially unrestricted contractions and expansions of the torso of the user associated with breathing.

6. A method for making an orthosis, comprising the steps of:

providing a laminate material comprising a flexible foam material and a substantially rigid plastic sheet material sandwiched between a pair of soft flexible sheet materials and bonded together to yield a unitary and substantially rigid laminate material;

forming a body support from the laminate material, the body support being formed by heating the laminate material under conditions of pressure to soften the laminate to a pliable state, cutting the laminate to a desired shape to yield a pattern corresponding to a desired shape of the body support, providing a form corresponding to a desired configuration of the body support and positioning the pattern on the form in a pliable state, applying a negative pressure to conform the pattern to the form, and cooling the conformed pattern to yield the body support.

7. The method of claim 6, wherein the step of cutting the laminate occurs prior to the step of heating the laminate under conditions of pressure.

8. The method of claim 6, wherein the step of cutting the laminate occurs after the step of heating the laminate under conditions of pressure.

9. The method of claim 6, wherein the step of applying a negative pressure to conform the pattern to the form, comprises applying a plastic bag around the form having the pattern thereon and applying a negative pressure to the bag.

10. The orthosis of claim 6, wherein the body support member is configured for placement around a torso of a user and has sufficient rigidity to serve a support function, while also having a degree of flexibility sufficient to permit substantially unrestricted contractions and expansions of the torso of the user associated with breathing.

* * * * *